United States Patent [19]
Dolfini et al.

[11] 4,155,905
[45] May 22, 1979

[54] 6-SUBSTITUTED PENICILLANIC ACID AND DERIVATIVES THEREOF

[75] Inventors: Joseph E. Dolfini, Princeton; Ekkehard Bohme, Hightstown, both of N.J.

[73] Assignee: E. R. Squibb & Sons, Inc., Princeton, N.J.

[21] Appl. No.: 276,548

[22] Filed: Jul. 31, 1972

Related U.S. Application Data

[63] Continuation-in-part of Ser. No. 108,952, Jan. 22, 1971, abandoned.

[51] Int. Cl.² ............................................. C07D 499/44
[52] U.S. Cl. .................................. 260/239.1; 424/271
[58] Field of Search ...................................... 260/239.1

[56] References Cited
U.S. PATENT DOCUMENTS

| | | | |
|---|---|---|---|
| 2,562,410 | 6/1951 | Behrens et al. | 260/239.1 |
| 3,780,033 | 12/1973 | Hazen | 260/243 C |
| 3,780,034 | 12/1973 | Christensen et al. | 260/243 C |

*Primary Examiner*—Nicholas S. Rizzo
*Attorney, Agent, or Firm*—Lawrence S. Levinson; Merle J. Smith; Stephen B. Davis

[57] ABSTRACT

Disclosed herein are penicillanic acids and derivatives thereof which are substituted in the 6-position, processes for preparing such compounds and the utility thereof. The compounds of the invention have been found to be useful as antibacterial agents.

14 Claims, No Drawings

6-SUBSTITUTED PENICILLANIC ACID AND DERIVATIVES THEREOF

This application is a continuation-in-part of Ser. No. 108,952, filed Jan. 22, 1971, now abandoned.

SUMMARY OF THE INVENTION

This invention relates to 6-substituted-6-aminopenicillanic acid having the following Formula I:

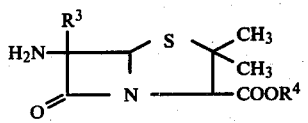

wherein $R^3$ is alkyl, aralkyl, alkylene alkyl, cycloalkyl or cycloalkylene and $R^4$ is hydrogen, lower alkyl, aralkyl, substituted alkyl, substituted aralkyl, trimethylsilyl, or cation. These compounds have been found to be useful as antibacterial agents and as intermediates in the preparation of 6-acylamino-6-substituted penicillanic acids and pharmaceutically acceptable salts thereof.

DESCRIPTION OF INVENTION

This invention relates to novel 6-substituted-6-amino penicillanic acid and derivatives thereof which are active as antibacterial agents and are valuable intermediates utilized in the preparation of the acylated derivatives. The 6-substituted-6-amino penicillanic acids and salts of this invention also possess antibacterial activity which is enhanced by acylation of the 6 amino group. In Formula I above the term pharmaceutically acceptable cation means an alkali metal (e.g., sodium and potassium), an alkaline earth metal (e.g., calcium and magnesium), ammonium, or an amine, such as a lower alkyl amine (e.g., methylamine), a di(lower alkyl)amine (e.g., diethylamine), a phenyl-lower alkylamine (e.g., benzylamine), a di(phenyl-lower alkyl)amine (e.g., dibenzylamine), or an alkylenediamine(e.g., N,N'-dibenzylethylenediamine), or the like.

Compounds of Formula I are prepared by reaction a Schiff's base of 6-aminopenicillanic acid of Formula II:

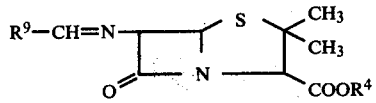

wherein $R^9$ is phenyl, X-substituted phenyl, lower alkyl or aralkyl (e.g., benzyl or phenethyl), wherein X is halogen (e.g., chloro, bromo), alkoxy, hydroxy, nitro, amine, or lower alkyl; with a compound having the Formula III:

$R^3$—L                          III wherein L is a leaving group such as halogen (e.g., chloro-, bromo-, and so forth), sulfonate, sulfate, methylsulfonyloxy, p-toluenesulfonyloxy, and $R^3$ is as defined herein.

This reaction is conducted in the presence of a base, such as triphenylmethyl sodium, sodium hydride, sodium hydroxide, potassium t-butoxide, sodium methoxide, etc.

Compounds of Formula III that may be utilized in the practice of the invention include methyl sulfate, ethyl sulfate, methyl p-toluenesulfonate, propyliodide, allylchloride, benzylchloride, hexylchloride, 1,2-dichloropropene-2, butylbromide, methyl iodide and so forth.

It is to be understood that the term lower alkyl and lower alkoxy in the formulae of the instant invention include straight and branched chain radicals of from 1 to about 8 carbons such as methyl, ethyl, propyl, isopropyl, butyl, isobutyl, t-butyl, amyl, methoxy, ethoxy, propoxy, isopropoxy, and the like. Further, it will be appreciated that certain of the compounds of this invention exist in different optically active forms. The various stereoisomeric forms as well as the racemic compounds are within the scope of this invention.

The term aryl is intended to include phenyl, α- and β-naphthyl, In addition, the term aryl is intended to encompass mono and disubstituted-phenyl, or α- and β-naphthyl groups wherein said substituents are halogen, hydroxy, amino, nitro and alkyl.

The term heterocyclyl, while intended to encompass the entire class, more specifically is intended to encompass the thiophene, isoxazole, oxadiazole, thiadiazole, pyridine, pyrazene, morpholine, quinoline, isoquinoline, tetrazole, furan, pyrrole and indole. The ring systems may be at various hydrogenated states, such as dihydrofuran and tetrahydroduran. In addition, the point of linkage may be at any of the possible ring positions and the ring systems may carry additional substituents such as alkyl, alkoxy, amino, nitro, halogen, etc.

Suitable compounds of Formula II include any Schiff's base of 6-APA (or a protected form thereof). When using this process, the preferred Schiff's bases are those formed with aldehydes which do not interfere with the alkylation reaction. Thus, although any of the Schiff's bases of 6-APA disclosed in U.S. Pat. No. 3,288,800 can be used, the preferred are those of the formula:

RCHO wherein R is phenyl, p-methoxyphenyl, m-nitrophenyl, halophenyl (e.g., p-chlorophenyl, m-fluorophenyl and o-bromophenyl), (lower alkoxy)phenyl (e.g., o-methoxyphenyl), carbo(lower alkoxy)phenyl (e.g., p-carbomethoxyphenyl, o-carboethoxyphenyl, p-carbohexyloxyphenyl, and m-carbobutoxyphenyl), o-n-propoxyphenyl, and p-n-hexyloxyphenyl), di(lower alkyl) aminophenyl [e.g., p-dimethylaminophenyl, o-diethylaminophenyl, p-(N-n-butyl-N-methylamino)phenyl, and m-di-n-pentylaminophenyl], naphthyl. The reaction in forming compounds of Formula II is preferably conducted in an inert organic solvent for the Schiff's base reactant, such as methylene chloride, benzene, dimethoxyethane, dioxane and chloroform.

Compounds of the Formula II can be used in either their salt form or in the form of an ester. Suitable salt forms include those with alkali metals (e.g., sodium and potassium), alkaline earth metals (e.g., calcium). Suitable esters include those formed with lower alkanols (e.g., methanol, ethanol and tert.-butanol), cycloalkanols (e.g., cyclohexanol and cyclopentanol), carbocyclic aryl alcohols (e.g. phenol and 2-naphthol), carbocyclic ar(lower alkanols), (e.g., benzyl alcohol, benzhydrol, 1-naphthylmethyl alcohol and 2-phenylethanol), trimethylsilyl, lower alkanoyl(lower alkanols) (e.g., hydroxyacetone and pivaloylmethanol), carbocyclic aroyl(lower alkanols) (e.g., benzoylmethanol, 2-benzoylethanol and 2-naphthylcarbonylmethanol), cycloalkylcarbonyl(lower alkanols) (e.g., hydroxymethylcyclohexylketone), lower alkanoyloxy (lower alkanols)

(e.g., pivaloyloxymethanol), and substituted derivatives of any of the above, such as lower alkyl (e.g., methyl and ethyl), lower alkoxy (e.g., methoxy and butoxy), halo (e.g., chloro, fluoro and bromo), and nitro derivatives, as exemplified by 2,2,2-trichloroethanol, 2-bromoethanol, p-nitrophenol, p-methoxyphenol, p-methoxybenzyl alcohol, p,p'-dimethoxybenzhydrol, 2-dimethylamino ethanol, p-nitrobenzoylmethanol and p-methoxybenzoylmethanol. In addition the free acid may be utilized with the reaction being carried out with excess of base thus forming the salt in situ.

The reaction of Compound II with Compound III yields a compound of Formula IV:

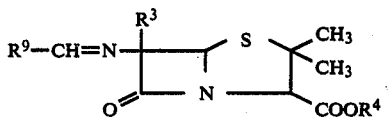

which can then be converted to compounds of Formula I by hydrolysis in the presence of a mild aqueous acid, such as hydrochloric, sulfuric, formic, trifluoroacetic and acetic acid, p-toluene-sulphonic acid to yield the 6-substituted-6-aminopenicillanic acid of Formula I.

As stated above compounds of Formula I are valuable intermediates in the formation of acylated compounds having the Formula V:

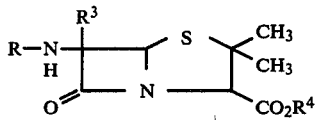

wherein $R^3$ and $R^4$ are as defined herein and R is acyl. Acyl in this invention is defined as:

(a) $R^2(CH_2)_nCO-$ where $R^2$ is phenyl, nitrophenyl, chlorophenyl, bromophenyl, lower alkyl phenyl, lower alkoxy phenyl, cycloalkyl or thienyl, and n is 0 or an integer from 1 to 4;

(b) $R^5CO-$ where $R^5$ contains from 2 to 7 carbon atoms and is alkyl, alkylthioalkyl or alkoxyalkoxyalkyl;

(c) $R^6CO-$ where $R^6$ contains from 2 to 7 carbon atoms and is alkenyl, alkylthioalkenyl, alkenylthioalkyl, alkoxyalkenyl or alkenyloxyalkyl;

(d) $R^2X_1(CH_2)_nCO-$ where $R^2$ and n are as defined above and $X_1$ is oxygen or sulphur.

(e) $R^2(CH_2)_nS(CH_2)_mCH_2CO-$ where $R^2$ and n are as defined above and m is 0 or an integer from 1 to 4;

(f) $R^7(CH_2)_nCO-$ where $R^7$ is carbocyclic or substituted carbocyclic (e.g., lower alkyl dihydrocyclohexyl, lower alkoxy dihydrocyclohexyl such as 2,4-dimethyl-2,4-dihydrocyclohexyl, and 2-propoxy-2,4-dihydrocyclohexyl), aryl, hetercyclyl, aryloxy, arylthio, and alkyloxy and n is an integer from 0, 1 to 4;

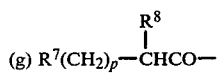

where $R^7$ is as defined herein, $R^8$ is alkyl, amino, ureido, carboxy, sulfonyl, phosphonyl, hydrogen, hydroxy, chloro, bromo, or iodo; p is an integer from 0, 1 to 3, and

where $R^2$, $R^8$ and p are as defined above.

The formation of compounds of general Formula V may, for example, be effected by one of the following methods:

(a) Reaction of the compound of general Formula I with an acid chloride, or acid anhydride, active ester, acid azide, etc. in aqueous or organic solution.

(b) Reaction of the compound of general Formula I with a mixed anhydride of an acid corresponding to the desired acyl group and another acid, the mixed anhydride being formed by reaction of the acid corresponding to the desired acyl group with an alkyl haloformate, if desired formed in situ; the reaction with the mixed anhydride preferably being conducted in solution in an anhydrous, inert solvent in the presence of an acid binding agent e.g., a tertiary amine.

(c) Reaction of the compound of Formula I with the activated form of a carboxylic acid formed by reaction with carbonyl-di-imidazole or dicyclohexylcarbodiimide or similar activating agent.

The compounds of this invention have antibiotic activity against gram-positive organisms, such as *Staphylococcus aureus* and *Streptococcus pyrogenes*. They may be used as antibacterial agents in a prophylactic manner, e.g., in cleaning or disinfecting compositions, or otherwise to combat infections due to organisms such as those named above, and in general may be utilized in a manner similar to penicillin G and other penicillins. For example, a compound of Formula I may be used in various animal species in an amount of about 0.1 to 100 mg/kg daily, orally or parenterally, in single or two to four divided doses to treat infections of bacterial origin. In cleaning or disinfecting compositions, e.g., in farm or dairy equipment, a concentration of about 0.01 to 1% by weight of such compounds admixed with, suspended or dissolved in conventional inert dry or aqueous carriers by application by washing or spraying may be utilized.

The following examples illustrate the invention (all temperatures being in degrees Centigrade, unless otherwise stated):

EXAMPLE 1

N-Benzylidene-6-aminopenicillanic Acid 73.8 Mmoles N-benzylidene-6-aminopenicillanic acid, t-octylamine salt is added to 240 ml methylene chloride cooled to 0°-5° C. (water bath). After dispersion 158.5 mmoles benzaldehyde are added, followed by the addition of an 8 ml tetrahydrofuran solution containing 76.2 mmoles trifluoroacetic acid. During the course of this addition, the reaction mixture gradually clarifies to finally form a clear, slightly yellow solution. The reaction mixture is allowed to reach room temperature and concentrated to one-third its volume in vacuo at a temperature not exceeding 30° C. On cooling the desired product crystallized out in 82 mole %.

EXAMPLE 2

Salicylidene 6-APA 200 mg of a solution of 6-aminopenicillanic acid is neutralized with 40% sodium hydroxide to a pH of 3.5 and 2 ml of salicylaldehyde is added. The mixture is agitated one hour at room temperature and allowed to stand at 5°–10° for an additional hour. The oil which forms on the bottom is separated by decantation and centrifugation. This oil is salicylidene 6-aminopenicillanic acid.

EXAMPLES 3–5

By following the procedure of Example 2 and substituting in place of the salicylaldehyde an equivalent amount of:
o-nitrobenzaldehyde,
m-chlorobenzaldehyde, and
p-methoxybenzaldehyde,
the products obtained are:
N-o-nitrobenzyledene-6-aminopenicillanic acid,
N-m-chlorobenzyledene-6-aminopenicillanic acid, and
N-p-methoxybenzyledene-6-aminopenicillanic acid.

EXAMPLE 6

Benzyl ester of N-benzylidene-6-aminopenicillanic acid

Treatment of a 0.1 molar solution of N-benzylidene-6-aminopenicillanic acid with one equivalent of phenyl diazomethane in ether (Overberger and Anselme, J. ORG. CHEM., 28, 592 [1963]; Idem, J. AM. CHEM. SOC., 86, 658 [1954]) for one hour, followed by evaporation deposits the product.

EXAMPLE 7

Diphenylmethyl ester of N-benzylidene-6-aminopenicillanic acid

Substitution of one equivalent of diphenyldiazomethane for the solution of phenyl diazomethane in Example 6 gives the desired product.

EXAMPLE 8

Trichloroethyl ester of N-benzylidene-6-aminopenicillanic acid

The Schiff base of Example 1 (10.0 g) is dissolved in 150 ml of dichloromethane containing pyridine (5.2 g). Trichloroethanol 9.84 g is added followed by 6.79 g dicyclohexylcarbodiimide and the mixture stirred for two hours at room temperature. Precipitation of dicyclohexylurea occurs quickly. After two hours the precipitate is filtered off. The filtrate is diluted with dichloromethane and washed twice with an equal volume of water, first at pH 3.5, then at pH 7.2. It is then washed with saturated sodium chloride, dried over anhydrous magnesium sulfate, and stripped to dryness in vacuo. Wt. of yellow oil = 15.6 g.

The product is crystallized by dissolving it in 5 ml of ether and adding hexane to the warm solution until slightly turbid upon cooling.

EXAMPLE 9

Methyl ester of N-benzylidene-6-amino penicillanic acid

By treating a dioxane solution of the product of Example 1 with excess ethereal diazomethane, followed by evaporation of the solvent, the desired product is obtained. Trituration with hexane gives a powder.

EXAMPLE 10

6-Amino-6-methyl penicillanic acid

A solution of the benzaldehyde Schiff base 0.010 mole of 6-APA of Example 1 in 50 ml of dimethoxyethane is chilled to 0° C. under nitrogen; 0.020 mole of sodium hydride powder (mineral oil dispersion) is added, followed by 0.030 mole (excess) methyl iodide. The solution is rapidly stirred until hydrogen evolution is slowed or stops. Thin layer chromatography can be used to maintain disappearance of starting material and formation of the desired product. The reaction mixture is diluted with 100 ml water and the pH adjusted to 2.5 (at 0° C.). The reaction mixture is filtered and extracted with 2 portions of ether. The pH is readjusted to 4.5, and concentrated in vacuo if necessary, to precipitate the product.

EXAMPLE 11

N-Benzylidene-6-amino-6-methylpenicillanic acid, methyl ester 12.5 Meq. N-benzylidene-6-amino-6-penicillanic acid, methyl ester are dissolved in 2 ml dry DME under nitrogen at −5° C. Then a 20-fold excess methyl iodide is added along with 12.5 meq. sodium hydride. The reaction mixture turns yellow after a few minutes of stirring at that low temperature. After 3 hours, thin layer chromatography on silica gel, showed no more starting material. The reaction mixture is diluted with chloroform, washed with water, dried over magnesium sulphate and evaporated in vacuo to give 5.05 grams of a brown oil. This was recrystallized from hexane-dichloromethane to give 6.6 meq. 6-benzalimino-6-α-methylpenicillanic acid, methyl ester; chromatography of the mother liquors on silica gel led to the isolation of the β-6-methyl epimer.

EXAMPLE 12

N-Benzylidene-6-amino-6-methylpenicillanic acid, benzyl ester

Substitution of 12.5 meq. of the benzyl ester of 6-benzyliminopenicillanic acid acid in Example 11 for the methyl ester leads to the desired product.

EXAMPLE 13

N-Benzylidene-6-amino-6-methylpenicillanic acid, benzhydryl ester

By substituting 12.5 meq. of the benzhydryl ester for the methyl ester of Example 11, the desired product is obtained.

EXAMPLE 14

6-Amino-6-methylpenicillanic acid, methyl ester 5.1 Meq. 6-benzalimino-6-methylpenicillanic acid, methyl ester are hydrolyzed in a 50:50 mixture of acetone and 0.1 N aqueous hydrochloric acid for 10 minutes. The reaction mixture is then diluted with water and washed with chloroform. The acidic layer is then basified and extracted with chloroform. This latter chloroform layer is dried over magnesium sulphate and evaporated to dryness in vacuo. To give 4 meq. 6-amino-6-methylpenicillanic acid, methyl ester. MP 94°–95°.

EXAMPLE 15

6-Amino-6-methylpenicillanic acid, benzyl ester

Substituting 5.1 meq. of the product of Example 12 for the substrate of Example 14, and following the procedure therein, the desired product is obtained.

EXAMPLE 16

6-Amino-6-methylpenicillanic acid, benzhydryl ester

Substituting 5.1 meq. of the product of Example 13 for the substrate of Example 10, and following the procedure therein, the desired product is obtained.

EXAMPLE 17

6-Phenylacetamido-6-methylpenicillanic acid, methyl ester 2.25 Meq. 6-amino-6-methylpenicillanic acid, methyl ester are dissolved in 30 ml. chloroform, and cooled to ice-bath temperature under nitrogen. Then 2.25 meq. triethylamine are added followed by the addition of 2.25 meq. phenylacetylchloride. The reaction is allowed to proceed for two hours at ice-bath temperatures and under nitrogen. The solution is diluted with chloroform, washed with a solution at pH 7.2, washed with water, dried over magnesium sulphate, and evaporated to dryness to give 1.1 meq. of 6-phenylacetamido-6-methylpenicillanic acid, methyl ester as a clear oil which crystallizes on standing.

EXAMPLE 18

6-Phenylacetamido-6-methylpenicillanic acid (a) By hydrolysis; 1 mmole of the 6-(phenylacetamido)-6-methylpenicillanic acid, methyl ester in 10 ml. 95% ethanol is treated with one ml. of 1N NaOH at room temperature for 6 hours with stirring; the alcohol is evaporated at reduced pressure. The residue is dissolved in water and pH adjusted to 7.5 if necessary. The aqueous solution is washed with ethyl acetate, filtered and acidified to pH 4 at 0° C. to precipitate the product.

(b) The product of Example 10 obtained by using methyl iodide as a solution with triethylamine in 1:1 water/acetone at 0° C. is treated with one equivalent of phenylacetyl chloride, with triethylamine being added to maintain pH at 6.5 to 7.5. When no further pH change is noted the reaction is worked up as in part (a) to give the desired product.

(c) A suspension of the t-octyl amine salt (0.1 mol.) of the benzaldehyde Schiff base of 6-APA in 100 ml of dimethoxyethane is treated with 10.8 g of trimethyl silyl chloride at 10° C. for two hours. The reaction mix is filtered and 0.1 eq. of sodium hydride as a mineral oil dispersion is added followed immediately by 28 g of methyl iodide. After two to three hours, the reaction mix is diluted with 250 ml $H_2O$ and acidified to pH 2. After 20 minutes the result is filtered and the filtrate washed with ether. Adjusting the pH of the solution to 7 with triethylamine gives a solution of 6-methyl-6-APA which can be acylated with 0.10 mol. phenylacetyl chloride as in 18b to give the product.

Similarly, by substituting an equivalent amount of phenoxyacetyl chloride for the phenylacetyl chloride, one obtains 6-phenoxyacetyl-6-methylpenicillanic acid.

EXAMPLE 19

6-Amino-6-benzylpenicillanic acid

6-Amino-6-benzylpenicillanic acid is prepared by using benzyl chloride in lieu of methyl iodide of Example 10.

EXAMPLE 20

N-Benzylidene-6-amino-6-benzylpenicillanic acid, methyl ester

N-Benzylidene-6-amino-6-benzylpenicillanic acid, methyl ester is prepared by the procedure of Example 11, but using an equivalent amount of benzyl chloride in place of methyl iodide.

EXAMPLE 21

6-Amino-6-benzylpenicillanic acid, methyl ester

6-Amino-6-benzylpenicillanic acid, methyl ester is prepared by using the product of Example 20 to replace the substrate 6-methyl compound of Example 14.

EXAMPLE 22

6-Phenylacetamido-6-benzylpenicillanic acid, methyl ester

6-Phenylacetamido-6-benzylpenicillanic acid, methyl ester is prepared by using the product of Example 19 for the substrate in Example 17.

EXAMPLE 23

6-Phenylacetamido-6-benzylpenicillanic acid

6-Phenylacetamido-6-benzylpenicillanic acid is prepared by the procedures of Example 18, substituting the corresponding 6-benzyl compound for the 6-methyl compounds.

Similarly, by also substituting an equivalent amount of phenoxyacetyl chloride for the phenylacetyl chloride, one obtains 6-phenoxyacetyl-6-benzylpenicillanic acid.

EXAMPLES 24–46

6-Acylamino-6-methylpenicillanic acids

By following the procedure of Example 18b and substituting an equivalent amount of the corresponding acid chloride of the following carboxylic acids:

α-(2-chlorophenoxy)propionic acid,
α-(4-sulfamylphenoxy)-n-butyric acid,
α-(3,4-dimethoxyphenoxy)-n-pentanoic acid,
α-(3-methylphenoxy)isovaleric acid,
α-(4-methylthiophenoxy)propionic acid,
α-(4-dimethylaminophenoxy)-n-hexanoic acid,
α-(2-methoxyphenoxy)-n-decanoic acid,
α-(2,4-dichlorophenoxy)phenylacetic acid,
α-(2-nitrophenoxy)-β-phenylpropionic acid,
α-(2-acetamidophenoxy)-γ-phenylbutyric acid,
α-(2,4-dimethylphenoxy)-n-butyric acid,
α-(4-isopropylphenoxy)propionic acid,
α-(3-bromophenoxy)-n-butyric acid,
α-(2-iodophenoxy)phenylacetic acid,
α-(2-diethylaminophenoxy)isovaleric acid,
α-(3,5-dichlorophenoxy)isohexanoic acid,
α-(4-cyclohexylphenoxy)propionic acid,
α-phenoxy-isovaleric acid,
α-phenoxy-n-decanoic acid,
α-phenoxy-γ-phenylbutyric acid,
α-(2-benzylphenoxy)-n-butyric acid,
α-(2-trifluoromethylphenoxy)propionic acid, and
α-(4-fluorophenoxy)propionic acid, the products obtained are
6-[α-(2-chlorophenoxy)propionamido]-6-methylpenicillanic acid,
6-[α-(4-sulfamylphenoxy)-n-butyramido]-6-methylpenicillanic acid, 6-[α-(3,4-dimethoxyphenoxy)-n-pentanoamido]-6-methylpenicillanic acid,
6-[α-(3-methylphenoxy)isovaleramido]-6-methylpenicillanic acid,
6-[α-(4-methylthiophenoxy)propionamido]-6-methylpenicillanic acid,
6-[α-(4-dimethylaminophenoxy)-n-hexanoamido]-6-methylpenicillanic acid
6-[α-(2-methoxyphenoxy)-n-decanoamido]-6-methylpenicillanic acid,
6-[α-(2,4-dichlorophenoxy)phenylacetamido]-6-methylpenicillanic acid,
6-[α-(2-nitrophenoxy)-β-phenylpropionamido]-6-methylpenicillanic acid,
6-[α-(2-acetamidophenoxy)-γ-phenylbutyramido]-6-methylpenicillanic acid,
6-[α-(2,4-dimethylphenoxy)-n-butyramido]-6-methylpenicillanic acid,
6-[α-(4-isopropylphenoxy)propionamido]-6-methylpenicillanic acid,
6-[α-(3-bromophenoxy)-n-butyramido]-6-methylpenicillanic acid,
6-[α-(2-iodophenoxy)phenylacetamido]-6-methylpenicillanic acid,
6-[α-(2-diethylaminophenoxy)isovaleramido]-6-methylpenicillanic acid,
6-[α-(3,5-dichlorophenoxy)isohexanoamido]-6-methylpenicillanic acid,
6-[α-(4-cyclohexylphenoxy)propionamido]-6-methylpenicillanic acid,
6-[α-phenoxy-isovaleramido]-6-methylpenicillanic acid,
6-[α-phenoxy-n-decanoamido]-6-methylpenicillanic acid,
6-[α-phenoxy-γ-phenylbutyramido]-6-methylpenicillanic acid,
6-[α-(2-benzylphenoxy)-n-butyramido]-6-methylpenicillanic acid,
6-[α-(2-trifluoromethylphenoxy)propionamido]-6-methylpenicillanic acid, and
6-[α-(4-fluorophenoxy)propionamido]-6-methylpenicillanic acid, respectively.

EXAMPLES 47–76

By following the procedure of Example 18b and substituting an equivalent amount of the corresponding acid chloride of the following carboxylic acids:
α-phenylthiopropionic acid,
α-paranitrophenylthiopropionic acid,
α-parachlorophenylthiopropionic acid,
α-phenylthiobutyric acid,
α-phenylthiocaproic acid,
α-phenylthioisovaleric acid,
α-(4-t-butylphenylthio)propionic acid,
α-ortho-tolylthiopropionic acid,
α-ortho-nitrophenylthiopropionic acid,
α-parachlorophenylthiobutyric acid,
α-(3,4,5-trichlorophenylthio)propionic acid,
α-(3-trifluoromethylphenylthio)butyric acid,
α-parabromophenylthioisovaleric acid,
α-paraphenylphenylthiopropionic acid,
α-(4-methoxyphenylthio)caproic acid,
α-(4-cyclohexylphenylthio)butyric acid,
α-phenylthio-α-cyclohexylacetic acid,
α-phenylthio-α-cyclopentylacetic acid,
α-(2,4-dichlorophenylthio)caproic acid,
α-(2,4-diisoamylphenylthio)propionic acid,
α-(4-benzylphenylthio)propionic acid,
α-(4-sulfamylphenylthio)butyric acid,
α-(2-allyloxyphenylthio)propionic acid,
α-(4-allylphenylthio)isovaleric acid,
α-(4-dimethylaminophenylthio)propionic acid,
α-(2,5-dichlorophenylthio)butyric acid,
α-(2-iodophenylthio)propionic acid,
α-(2-acetamidophenylthio)propionic acid,
α-(4-diethylaminophenylthio)propionic acid, and
α-(3-fluorophenylthio)butyric acid, the products obtained are
6-(α-phenylthiopropionamido)-6-methylpenicillanic acid,
6-(α-paranitrophenylthiopropionamido)-6-methylpenicillanic acid,
6-(α-parachlorophenylthiopropionamido)-6-methylpenicillanic acid,
6-(α-phenylthiobutyramido)-6-methylpenicillanic acid,
6-(α-phenylthiocaproamido)-6-methylpenicillanic acid,
6-(α-phenylthioisovaleramido)-6-methylpenicillanic acid,
6-[α-(4-t-butylphenylthio)propionamido]-6-methylpenicillanic acid,
6-[α-ortho-tolylthiopropionamido]-6-methylpenicillanic acid,
6-(α-ortho-nitrophenylthiopropionamido)-6-methylpenicillanic acid,
6-(α-parachlorophenylthiobutyramido)-6-methylpenicillanic acid,
6-[α-(3,4,5-trichlorophenylthio)propionamido]-6-methylpenicillanic acid,
6-[α-(3-trifluoromethylphenylthio)butyramido]-6-methylpenicillanic acid,
6-(α-parabromophenylthioisovaleramido)-6-methylpenicillanic acid,
6-(α-paraphenylphenylthiopropionamido)-6-methylpenicillanic acid,
6-[α-(4-methoxyphenylthio)caproamido]-6-methylpenicillanic acid,
6-[α-(4-cyclohexylphenylthio)butyramido]-6-methylpenicillanic acid,
6-(α-phenylthio-α-cyclohexylacetamido)-6-methylpenicillanic acid,
6-(α-phenylthio-α-cyclopentylacetamido)-6-methylpenicillanic acid,
6-[α-(2,4-dichlorophenylthio)caproamido]-6-methylpenicillanic acid,
6-[α-(2,4-diisoamylphenylthio)propionamido]-6-methylpenicillanic acid,
6-[α-(4-benzylphenylthio)propionamido]-6-methylpenicillanic acid,
6-[α-(4-sulfamylphenylthio)butyramido]-6-methylpenicillanic acid,
6-[α-(2-allyloxyphenylthio)propionamido]-6-methylpenicillanic acid,
6-[α-(4-allylphenylthio)isovaleramido]-6-methylpenicillanic acid,
6-[α-(4-dimethylaminophenylthio)propionamido]-6-methylpenicillanic acid,
6-[α-(2,5-dichlorophenylthio)butyramido]-6-methylpenicillanic acid,
6-[α-(2-iodophenylthio)propionamido]-6-methylpenicillanic acid,
6-[α-(2-acetamidophenylthio)propionamido]-6-methylpenicillanic acid,
6-[α-(4-diethylaminophenylthio)propionamido]-6-methylpenicillanic acid, and
6-[α-(3-fluorophenylthio)butyramido]-6-methylpenicillanic acid, respectively.

EXAMPLES 77–90

By following the procedure of Example 18b and substituting an equivalent amount of the corresponding acid chloride of the following carboxylic acids D,L-α-amino-(3-thienyl)acetic acid,
α-amino-5-ethyl-2-thienyl)acetic acid,
α-amino-(5-methyl-2-thienyl)acetic acid,
α-amino-(5-t-butyl-2-thienyl)acetic acid,
α-amino-(2,5-dimethyl-3-thienyl)acetic acid,
α-amino-(5-chloro-2-thienyl)acetic acid,
α-amino-(5-bromo-2-thienyl)acetic acid,
α-amino-(5-phenyl-3-chloro-2-thienyl)acetic acid,
α-amino-3,5-dimethyl-2-thienyl)acetic acid,
α-amino-(5-cyclohexyl-2-thienyl)acetic acid,
α-amino-(5-diethylamino-2-thienyl)acetic acid,
α-amino-(4-methylsulfonyl-2-thienyl)acetic acid,
α-amino-(3-ethylthio-2-thienyl)acetic acid, and
α-amino-(4-cycloheptyloxy-2-thienyl)acetic acid, the products obtained are D,L-6-[α-amino-(3-thienyl)acetamido]-6-methylpenicillanic acid,
6-[α-amino-(5-ethyl-2-thienyl)acetamido]-6-methylpenicillanic acid,
6-[α-amino-(5-methyl-2-thienyl)acetamido]-6-methylpenicillanic acid,
6-[α-amino-(5-t-butyl)-2-thienyl)acetamido]-6-methylpenicillanic acid,
6-[α-amino-(2,5-dimethyl-3-thienyl)acetamido]-6-methylpenicillanic acid,
6-[α-amino-(5-chloro-2-thienyl)acetamido]-6-methylpenicillanic acid,
6-[α-amino-(5-bromo-2-thienyl)acetamido]-6-methylpenicillanic acid,
6-[α-amino-(5-phenyl-3-chloro-2-thienyl)acetamido]-6-methylpenicillanic acid,
6-[α-amino-(3,5-dimethyl-2-thienyl)acetamido]-6-methylpenicillanic acid,
6-[α-amino-(5-cyclohexyl-2-thienyl)acetamido]-6-methylpenicillanic acid,
6-[α-amino-(5-diethylamino-2-thienyl)acetamido]-6-methylpenicillanic acid,
6-[α-amino-(4-methylsulfonyl-2-thienyl)acetamido]-6-methylpenicillanic acid,
6-[α-amino-(3-ethylthio-2-thienyl)acetamido]-6-methylpenicillanic acid, and
6-[α-amino-(4-cycloheptyloxy-2-thienyl)acetamido]-6-methylpenicillanic acid, respectively.

EXAMPLES 91–113

By following the procedure of Example 18b and substituting an equivalent amount of the corresponding acid chloride of the following carboxylic acids α-amino-p-chlorophenylacetic acid,
α-amino-p-methoxyphenylacetic acid,
D-(−)-α-aminophenylacetic acid,
α-amino-4-diethylaminophenylacetic acid,
α-amino-4-trifluoromethylphenylacetic acid,
α-amino-2,4-dibromophenylacetic acid,
α-amino-2-nitrophenylacetic acid,
α-amino-3-methylphenylacetic acid,
α-amino-4-sulfamylphenylacetic acid,
α-amino-2-iodophenylacetic acid,
α-amino-4-t-butylphenylacetic acid,
α-amino-2-acetamidophenylacetic acid,
α-amino-3-nitrophenylacetic acid,
α-amino-3,4-dimethoxyphenylacetic acid,
α-amino-4-dimethylaminophenylacetic acid,
α-amino-2,4-dichlorophenylacetic acid,
α-amino-4-isopropylphenylacetic acid,
α-amino-3-bromophenylacetic acid,
α-amino-3-iodophenylacetic acid,
α-amino-2-diethylaminophenylacetic acid,
α-amino-2-trifluoromethylphenylacetic acid,
α-amino-4-fluorophenylacetic acid, and
α-amino-3,4,5-trifluoromethylphenylacetic acid, the products obtained are 6-(α-amino-p-chlorophenylacetamido)-6-methylpenicillanic acid,
6-(α-amino-p-methoxyphenylacetamido)-6-methylpenicillanic acid,
6-[D-(−)-α-aminophenylacetamido]-6-methylpenicillanic acid,
6-(α-amino-4-diethylaminophenylacetamido)-6-methylpenicillanic acid,
6-(α-amino-4-trifluoromethylphenylacetamido)-6-methylpenicillanic acid,
6-(α-amino-2,4-dibromophenylacetamido)-6-methylpenicillanic acid,
6-(α-amino-2-nitrophenylacetamido)-6-methylpenicillanic acid,
6-(α-amino-3-methylphenylacetamido)-6-methylpenicillanic acid,
6-(α-amino-4-sulfamylphenylacetamido)-6-methylpenicillanic acid,
6-(α-amino-2-iodophenylacetamido)-6-methylpenicillanic acid,
6-(α-amino-4-t-butylphenylacetamido)-6-methylpenicillanic acid,
6-(α-amino-2-acetamidophenylacetamido)-6-methylpenicillanic acid,
6-(α-amino-3-nitrophenylacetamido)-6-methylpenicillanic acid,
6-(α-amino-3,4-dimethoxyphenylacetamido)-6-methylpenicillanic acid,
6-(α-amino-4-dimethylaminophenylacetamido)-6-methylpenicillanic acid,
6-(α-amino-2,4-dichlorophenylacetamido)-6-methylpenicillanic acid,
6-(α-amino-4-isopropylphenylacetamido)-6-methylpenicillanic acid,
6-(α-amino-3-bromophenylacetamido)-6-methylpenicillanic acid,
6-(α-amino-3-iodophenylacetamido)-6-methylpenicillanic acid,
6-(α-amino-2-diethylaminophenylacetamido)-6-methylpenicillanic acid,
6-(α-amino-2-trifluoromethylphenylacetamido)-6-methylpenicillanic acid,
6-(α-amino-4-fluorophenylacetamido)-6-methylpenicillanic acid, and
6-(α-amino-3,4,5-trifluoromethylphenylacetamido)-6-methylpenicillanic acid, respectively.

EXAMPLES 114–184

By following the procedure of Example 18b and substituting an equivalent amount of the following acid chloride:
benzoyl chloride
3,5-dinitrobenzoyl chloride,
2-chlorobenzoyl chloride,
2-methylbenzoyl chloride,
4-aminobenzoyl chloride,
4-nitrobenzoyl chloride,
4-hydroxybenzoyl chloride,
3,4,5-trimethoxybenzoyl chloride, 4-methylbenzoyl chloride,
4-chlorobenzoyl chloride,
3,4-dichlorobenzoyl chloride,
3-nitrobenzoyl chloride,
2,4,6-trimethoxybenzoyl chloride,
2-hydroxybenzoyl chloride,
4-ethoxybenzoyl chloride,
2,6-dimethoxybenzoyl chloride,
2,4,6-trimethylbenzoyl chloride,
2,6-dichlorobenzoyl chloride,
2,6-diethoxybenzoyl chloride,
2,6-di-n-butoxybenzoyl chloride,
2,6-dibenzyloxybenzoyl chloride,
2,3,6-trimethoxybenzoyl chloride,
2,4,6-tribromobenzoyl chloride,
2,6-di-n-propoxybenzoyl chloride,
2,6-dimethoxy-4-methylbenzoyl chloride,
4,6-diethyl-2-methoxybenzoyl chloride,
6-ethoxy-2-methoxybenzoyl chloride,
2-methylthiobenzoyl chloride,
2-benzylthiobenzoyl chloride,
2-phenoxybenzoyl chloride,
2-phenylbenzoyl chloride,
2-methoxybenzoyl chloride,
4-sulfamylbenzoyl chloride,
3,4-dimethoxybenzoyl chloride,
4-methoxybenzoyl chloride,
3-methylbenzoyl chloride,
3-dimethylaminobenzoyl chloride,
2-methoxybenzoyl chloride,
2-chloro-3,4,5-trimethoxybenzoyl chloride,
2,4-dichlorobenzoyl chloride,
2-nitrobenzoyl chloride,
4-methylaminobenzoyl chloride,
2-acetamidobenzoyl chloride,
2,4-dimethylbenzoyl chloride,
2,4,5-trimethylbenzoyl chloride,
4-isopropylbenzoyl chloride,
3-bromobenzoyl chloride,
2-iodobenzoyl chloride,
2-ethylaminobenzoyl chloride,
2,5-dihydroxybenzoyl chloride,
4-hydroxy-3-methoxybenzoyl chloride,
4-allylbenzoyl chloride,
4-allyloxybenzoyl chloride,
2-trifluoromethylbenzoyl chloride,
4-fluorobenzoyl chloride,
2-phenylthiobenzoyl chloride,
2-benzylbenzoyl chloride,
2,6-dihydroxybenzoyl chloride,
2,6-diacetoxybenzoyl chloride,
2,6-dimethylthiobenzoyl chloride,
2,4,6-trinitrobenzoyl chloride,
2,6-diacetamidobenzoyl chloride,
2,6-dibromobenzoyl chloride,
2,6-dimethylbenzoyl chloride,
2,6-diethylbenzoyl chloride,
2,6-diisopropylbenzoyl chloride,
2,6-diallyloxybenzoyl chloride,
3-bromo-2,6-dimethoxybenzoyl chloride,
4-chloro-2,6-dimethoxybenzoyl chloride,
2-chloro-6-nitrobenzoyl chloride, and
2-hydroxy-6-methoxybenzoyl chloride,
the products obtained are
6-(benzamido)-6-methylpenicillanic acid,
6-(3,5-dinitrobenzamido)-6-methylpenicillanic acid,
6-(2-chlorobenzamido)-6-methylpenicillanic acid,
6-(2-methylbenzamido)-6-methylpenicillanic acid,
6-(4-aminobenzamido)-6-methylpenicillanic acid,
6-(4-nitrobenzamido)-6-methylpenicillanic acid,
6-(4-hydroxybenzamido)-6-methylpenicillanic acid,
6-(3,4,5-trimethoxybenzamido)-6-methylpenicillanic acid,
6-(4-methylbenzamido)-6-methylpenicillanic acid,
6-(4-chlorobenzamido)-6-methylpenicillanic acid,
6-(3,4-dichlorobenzamido)-6-methylpenicillanic acid,
6-(3-nitrobenzamido)-6-methylpenicillanic acid,
6-(2,4,6-trimethoxybenzamido)-6-methylpenicillanic acid,
6-(2-hydroxybenzamido)-6-methylpenicillanic acid,
6-(4-ethoxybenzamido)-6-methylpenicillanic acid,
6-(2,6-dimethoxybenzamido)-6-methylpenicillanic acid,
6-(2,4,6-trimethylbenzamido)-6-methylpenicillanic acid,
6-(2,6-dichlorobenzamido)-6-methylpenicillanic acid,
6-(2,6-diethoxybenzamido)-6-methylpenicillanic acid,
6-(2,6-di-n-butoxybenzamido)-6-methylpenicillanic acid,
6-(2,6-dibenzyloxybenzamido)-6-methylpenicillanic acid,
6-(2,3,6-trimethoxybenzamido)-6-methylpenicillanic acid,
6-(2,4,6-tribromobenzamido)-6-methylpenicillanic acid,
6-(2,6-di-n-propoxybenzamido)-6-methylpenicillanic acid,
6-(2,6-dimethoxy-4-methylbenzamido)-6-methylpenicillanic acid,
6-(4,6-diethyl-2-methoxybenzamido)-6-methylpenicillanic acid,
6-(6-ethoxy-2-methoxybenzamido)-6-methylpenicillanic acid,
6-(2-methylthiobenzamido)-6-methylpenicillanic acid,
6-(2-benzylthiobenzamido)-6-methylpenicillanic acid,
6-(2-phenoxybenzamido)-6-methylpenicillanic acid,
6-(2-phenylbenzamido)-6-methylpenicillanic acid,
6-(2-methoxybenzamido)-6-methylpenicillanic acid,
6-(4-sulfamylbenzamido)-6-methylpenicillanic acid,
6-(3,4-dimethoxybenzamido)-6-methylpenicillanic acid,
6-(4-methoxybenzamido)-6-methylpenicillanic acid,
6-(3-methylbenzamido)-6-methylpenicillanic acid,
6-(3-dimethylaminobenzamido)-6-methylpenicillanic acid,
6-(2-methoxybenzamido)-6-methylpenicillanic acid,
6-(2-chloro-3,4,5-trimethoxybenzamido)-6-methylpenicillanic acid,
6-(2,4-dichlorobenzamido)-6-methylpenicillanic acid,
6-(2-nitrobenzamido)-6-methylpenicillanic acid,
6-(4-methylaminobenzamido)-6-methylpenicillanic acid,
6-(2-acetamidobenzamido)-6-methylpenicillanic acid,
6-(2,4-dimethylbenzamido)-6-methylpenicillanic acid,
6-(2,4,5-trimethylbenzamido)-6-methylpenicillanic acid,
6-(4-isopropylbenzamido)-6-methylpenicillanic acid,
6-(3-bromobenzamido)-6-methylpenicillanic acid,
6-(2-iodobenzamido)-6-methylpenicillanic acid,
6-(2-ethylaminobenzamido)-6-methylpenicillanic acid,
6-(2,5-dihydroxybenzamido)-6-methylpenicillanic acid,
6-(4-hydroxy-3-methoxybenzamido)-6-methylpenicillanic acid,
6-(4-allylbenzamido)-6-methylpenicillanic acid,
6-(4-allyloxybenzamido)-6-methylpenicillanic acid,
6-(2-trifluoromethylbenzamido)-6-methylpenicillanic acid,
6-(4-fluorobenzamido)-6-methylpenicillanic acid,
6-(2-phenylthiobenzamido)-6-methylpenicillanic acid,
6-(2-benzylbenzamido)-6-methylpenicillanic acid,
6-(2,6-dihydroxybenzamido)-6-methylpenicillanic acid, 6-(2,6-diacetoxybenzamido)-6-methylpenicillanic acid,
6-(2,6-dimethylthiobenzamido)-6-methylpenicillanic acid,
6-(2,4,6-trinitrobenzamido)-6-methylpenicillanic acid,
6-(2,6-diacetamidobenzamido)-6-methylpenicillanic acid,
6-(2,6-dibromobenzamido)-6-methylpenicillanic acid,
6-(2,6-dimethylbenzamido)-6-methylpenicillanic acid,
6-(2,6-diethylbenzamido)-6-methylpenicillanic acid,
6-(2,6-diisopropylbenzamido)-6-methylpenicillanic acid,
6-(2,6-diallyloxybenzamido)-6-methylpenicillanic acid,
6-(3-bromo-2,6-dimethoxybenzamido)-6-methylpenicillanic acid,
6-(4-chloro-2,6-dimethoxybenzamido)-6-methylpenicillanic acid,
6-(2-chloro-6-nitrobenzamido)-6-methylpenicillanic acid, and
6-(2-hydroxy-6-methoxybenzamido)-6-methylpenicillanic acid, respectively.

EXAMPLES 185–195

By following the procedure of Example 18b and substituting an equivalent amount of the following acid chloride:
(4-nitrophenyl)acetyl chloride,
(4-bromophenyl)acetyl chloride,
(4-t-butylphenyl)acetyl chloride,
(4-trifluoromethylphenyl)acetyl chloride,
(3-fluorophenyl)acetyl chloride,
(4-sulfamylphenyl)acetyl chloride,
(2-benzylphenyl)acetyl chloride,
(3-methoxyphenyl)acetyl chloride,
(2-iodophenyl)acetyl chloride,
(3-diethylaminophenyl)acetyl chloride, and
(2,4-diisoamylphenyl)acetyl chloride,
the products obtained are
6-[α-(4-nitrophenyl)acetamido]-6-methylpenicillanic acid,
6-[α-(4-bromophenyl)acetamido]-6-methylpenicillanic acid,
6-[α-(4-t-butylphenyl)acetamido]-6-methylpenicillanic acid,
6-[α-(4-trifluoromethylphenyl)acetamido]-6-methylpenicillanic acid,
6-[α-(3-fluorophenyl)acetamido]-6-methylpenicillanic acid,
6-[α-(4-sulfamylphenyl)acetamido]-6-methylpenicillanic acid,
6-[α-(2-benzylphenyl)acetamido]-6-methylpenicillanic acid,
6-[α-(3-methoxyphenyl)acetamido]-6-methylpenicillanic acid,
6-[α-(2-iodophenyl)acetamido]-6-methylpenicillanic acid,
6-[α-(3-diethylaminophenyl)acetamido]-6-methylpenicillanic acid, and
6-[α-(2,4-diisoamylphenyl)acetamido]-6-methylpenicillanic acid, respectively.

EXAMPLES 196–243

By following the procedure of Example 18b and substituting an equivalent amount of the following acid chloride:
3-m-chlorophenyl-5-methyl-4-isoxazole-4-carbonyl chloride,
3-(2,4-dichlorophenyl)-5-methyl-4-isoxazole-4-carbonyl chloride,
3-(3,4-dichlorophenyl)-5-methyl-4-isoxazole-4-carbonyl chloride,
3-p-tolyl-5-methyl-4-isoxazole-4-carbonyl chloride,
3-o-nitrophenyl-5-methyl-4-isoxazole-4-carbonyl chloride,
3-m-nitrophenyl-5-methyl-4-isoxazole-4-carbonyl chloride,
3-p-nitrophenyl-5-methyl-4-isoxazole-4-carbonyl chloride,
3-p-bromophenyl-5-methyl-4-isoxazole-4-carbonyl chloride,
3-p-fluorophenyl-5-methyl-4-isoxazole-4-carbonyl chloride,
3-p-methylsulfonylphenyl-5-methyl-4-isoxazole-4-carbonyl chloride,
3-p-methoxyphenyl-5-methyl-4-isoxazole-4-carbonyl chloride,
3-p-trifluoromethylphenyl-5-methyl-4-isoxazole-4-carbonyl chloride,
3-o-methoxyphenyl-5-methyl-4-isoxazole-4-carbonyl chloride,
3-p-ethoxyphenyl-5-methyl-4-isoxazole-4-carbonyl chloride,
3-(3,4-dimethoxyphenyl)-5-methyl-4-isoxazole-4-carbonyl chloride,
3-p-dimethylaminophenyl-5-methyl-4-isoxazole-4-carbonyl chloride,
3-α-naphthyl-5-methyl-4-isoxazole-4-carbonyl chloride,
3-β-naphthyl-5-methyl-4-isoxazole-4-carbonyl chloride,
3-phenyl-5-ethyl-4-isoxazole-4-carbonyl chloride,
3-p-chlorophenyl-5-ethyl-4-isoxazole-4-carbonyl chloride,
3-phenyl-5-isopropyl-4-isoxazole-4-carbonyl chloride,
3-phenyl-5-methylmercapto-4-isoxazole-4-carbonyl chloride,
3-methyl-5-o-chlorophenyl-4-isoxazole-4-carbonyl chloride,
3-methyl-5-p-bromophenyl-4-isoxazole-4-carbonyl chloride,
3-methyl-5-o-iodophenyl-4-isoxazole-4-carbonyl chloride,
3-methyl-5-(2,4-dichlorophenyl)-4-isoxazole-4-carbonyl chloride,
3-methyl-5-m-nitrophenyl-4-isoxazole-4-carbonyl chloride,
3-methyl-5-p-tolyl-4-isoxazole-4-carbonyl chloride,
3-methyl-5-p-nitrophenyl-4-isoxazole-4-carbonyl chloride,
3-methyl-5-p-methoxyphenyl-4-isoxazole-4-carbonyl chloride,
3-methyl-5-p-ethoxyphenyl-4-isoxazole-4-carbonyl chloride,
3-methyl-5-(2,6-dimethoxyphenyl)-4-isoxazole-4-carbonyl chloride,
3-methyl-5-p-methylsulfonylphenyl-4-isoxazole-4-carbonyl chloride,
3-methyl-5-p-fluorophenyl-4-isoxazole-4-carbonyl chloride,
3-methyl-5-p-cyanophenyl-4-isoxazole-4-carbonyl chloride,
3-methyl-5-p-methylmercaptophenyl-4-isoxazole-4-carbonyl chloride,
3-methyl-5-p-dimethylaminophenyl-4-isoxazole-4-carbonyl chloride,
3-methyl-5-α-naphthyl-4-isoxazole-4-carbonyl chloride,
3-methyl-5-β-naphthyl-4-isoxazole-4-carbonyl chloride,
3-ethyl-5-phenyl-4-isoxazole-4-carbonyl chloride, 3-ethyl-5-p-chlorophenyl-4-isoxazole-4-carbonyl chloride,
3-isopropyl-5-phenyl-4-isoxazole-4-carbonyl chloride,
3-tert. butyl-5-methyl-4-isoxazole-4-carbonyl chloride,
3-methyl-5-p-trifluoromethylphenyl-4-isoxazole-4-carbonyl chloride,
3-methyl-5-cyclohexyl-4-isoxazole-4-carbonyl chloride,
3-cyclohexyl-5-methyl-4-isoxazole-4-carbonyl chloride,
3-α-furyl-5-methyl-4-isoxazole-4-carbonyl chloride, and
3-α-thienyl-5-methyl-4-isoxazole-4-carbonyl chloride,
the products obtained are
6-(3-m-chlorophenyl-5-methyl-4-isoxazoyl-amino)-6-methylpenicillanic acid,
6-(3-(2,4-dichlorophenyl)-5-methyl-4-isoxazolyl-amino)-6-methylpenicillanic acid,
6-(3-(3,4-dichlorophenyl)-5-methyl-4-isoxazolyl-amino)-6-methylpenicillanic acid,
6-(3-p-tolyl-5-methyl-4-isoxazolyl-amino)-6-methylpenicillanic acid,
6-(3-o-nitrophenyl-5-methyl-4-isoxazolyl-amino)-6-methylpenicillanic acid,
6-(3-m-nitrophenyl-5-methyl-4-isoxazolyl-amino)-6-methylpenicillanic acid,
6-(3-p-nitrophenyl-5-methyl-4-isoxazolyl-amino)-6-methylpenicillanic acid,
6-(3-p-bromophenyl-5-methyl-4-isoxazolyl-amino)-6-methylpenicillanic acid,
6-(3-p-fluorophenyl-5-methyl-4-isoxazolyl-amino)-6-methylpenicillanic acid,
6-(3-p-methylsulfonylphenyl-5-methyl-4-isoxazolyl-amino)-6-methylpenicillanic acid,
6-(3-p-methoxyphenyl-5-methyl-4-isoxazolyl-amino)-6-methylpenicillanic acid,
6-(3-p-trifluoromethylphenyl-5-methyl-4-isoxazolyl-amino)-6-methylpenicillanic acid,
6-(3-o-methoxyphenyl-5-methyl-4-isoxazolyl-amino)-6-methylpenicillanic acid,
6-(3-p-ethoxyphenyl-5-methyl-4-isoxazolyl-amino)-6-methylpenicillanic acid,
6-(3-(3,4-dimethoxyphenyl)-5-methyl-4-isoxazolyl-amino)-6-methylpenicillanic acid,
6-(3-p-dimethylaminophenyl-5-methyl-4-isoxazolyl-amino)-6-metnylpenicillanic acid,
6-(3-α-naphthyl-5-methyl-4-isoxazolyl-amino)-6-methylpenicillanic acid,
6-(3-β-naphthyl-5-methyl-4-isoxazolyl-amino)-6-methylpenicillanic acid,
6-(3-phenyl-5-ethyl-4-isoxazolyl-amino)-6-methylpenicillanic acid,
6-(3-p-chlorophenyl-5-ethyl-4-isoxazolyl-amino)-6-methylpenicillanic acid,
6-(3-phenyl-5-isopropyl-4-isoxazolyl-amino)-6-methylpenicillanic acid,
6-(3-phenyl-5-methylmercapto-4-isoxazolyl-amino)-6-methylpenicillanic acid,
6-(3-methyl-5-o-chlorophenyl-4-isoxazolyl-amino)-6-methylpenicillanic acid,
6-(3-methyl-5-p-bromophenyl-4-isoxazolyl-amino)-6-methylpenicillanic acid,
6-(3-methyl-5-o-iodophenyl-4-isoxazolyl-amino)-6-methylpenicillanic acid,
6-(3-methyl-5-(2,4-dichlorophenyl)-4-isoxazolyl-amino)-6-methylpenicillanic acid,
6-(3-methyl-5-m-nitrophenyl-4-isoxazolyl-amino)-6-methylpenicillanic acid,
6-(3-methyl-5-p-tolyl-4-isoxazolyl-amino)-6-methylpenicillanic acid,
6-(3-methyl-5-p-nitrophenyl-4-isoxazolyl-amino)-6-methylpenicillanic acid,
6-(3-methyl-5-p-methoxyphenyl-4-isoxazolyl-amino)-5-methylpenicillanic acid,
6-(3-methyl-5-p-ethoxyphenyl-4-isoxazoyl-6-methylpenicillanic acid,
6-(3-methyl-5-(2,6-dimethoxyphenyl)-4-isoxazolyl-amino)-6-methylpenicillanic acid,
6-(3-methyl-5-p-methylsulfonylphenyl-4-isoxazolyl-amino)-6-methylpenicillanic acid,
6-(3-methyl-5-p-fluorophenyl-4-isoxazolyl-amino)-6-methylpenicillanic acid,
6-(3-methyl-5-p-cyanophenyl-4-isoxazolyl-amino)-6-methylpenicillanic acid,
6-(3-methyl-p-methylmercaptophenyl-4-isoxazolyl-amino)-6-methylpencillanic acid,
6-(3-methyl-5-p-dimethylaminophenyl-4-isoxazolyl-amino)-6-methylpenicillanic acid,
6-(3-methyl-5-α-naphthyl-4-isoxazolyl-amino)-6-methylpenicillanic acid,
6-(3-methyl-5-β-naphthyl-4-isoxazolyl-amino)-6-methylpenicillanic acid,
6-(3-ethyl-5-phenyl-4-isoxazolyl-amino)-6-methylpenicillanic acid,
6-(3-ethyl-5-p-chlorophenyl-4-isoxazolyl-amino)-6-methylpenicillanic acid,
6-(3-isopropyl-5-phenyl-4-isoxazolyl-amino)-6-methylpenicillanic acid,
6-(P3-tert.butyl-5-methyl-4-isoxazolyl-amino)-6-methylpenicillanic acid,
6-(3-methyl-5-p-trifluoromethylphenyl-4-isoxazolyl-amino)-6-methylpenicillanic acid,
6-(3-methyl-5-cyclohexyl-4-isoxazolyl-amino)-6-methylpenicillanic acid,
6-(3-cyclohexyl-5-methyl-4-isoxazolyl-amino)-6-methylpenicillanic acid,
6-(3-α-furyl-5-methyl-4-isoxazolyl-amino)-6-methylpenicillanic acid,
6-(3-α-thienyl-5-methyl-4-isoxazolyl-amino)-6-methylpenicillanic acid, respectively.

EXAMPLES 244–258

By following the procedure of Example 18b and substituting an equivalent amount of the following acid chloride:
3,5-diphenyl-4-isoxazole-4-carbonyl chloride,
3-methyl-5-phenyl-4-isoxazole-4-carbonyl chloride,
3,5-dimethyl-4-isoxazole-4-carbonyl chloride,
5-benzyl-3-methyl-4-isoxazole-4-carbonyl chloride,
3-methyl-5-styryl-4-isoxazole-4-carbonyl chloride,
5-tert.butyl-3-phenyl-4-isoazole-4-carbonyl chloride,
5-(2-furyl)-3-methyl-4-isoxazole-4-carbonyl chloride,
3-methyl-5-(3',5'-dimethyl-4'-isoxazolyl)-4-isoxazole-4-carbonyl chloride,
3-methyl-5-(2-thienyl)-4-isoxazole-4-carbonyl chloride,
3-(p-chlorophenyl)-5-methyl-4-isoxazole-4-carbonyl chloride,
3-methyl-5-methylmercapto-4-isoxazole-4-carbonyl chloride, 5-(p-chlorophenyl)-3-methyl-4-isoxazole-4-carbonyl chloride,
3-methyl-5-(o-nitrophenyl)-4-isoxazole-4-carbonyl chloride,
5-isopropyl-3-methyl-4-isoxazole-4-carbonyl chloride, and
5-methyl-3-(p-chlorophenyl)-4-isoxazole-4-carbonyl chloride,
the products obtained are:

6-(3,5-diphenyl-4-isoxazolyl-amino)-6-methylpenicillanic acid,
6-(3-methyl-5-phenyl-4-isoxazolyl-amino)-6-methylpenicillanic acid,
6-(3,5-dimethyl-4-isoxazolyl-amino)-6-methylpenicillanic acid,
6-(5-benzyl-3-methyl-4-isoxazolyl-amino)-6-methylpenicillanic acid,
6-(3-methyl-5-styryl-4-isoxazolyl-amino)-6-methylpenicillanic acid,
6-(5-tert.butyl-3-phenyl-4-isoxazolyl-amino)-6-methylpenicillanic acid,
6-(5-(2-furyl)-3-methyl-4-isoxazolyl-amino)-6-methylpenicillanic acid,
6-(3-methyl-5-(3',5'-dimethyl-4'-isoxazolyl)-4-isoxazolyl-amino)-6-methylpenicillanic acid,
6-(3-methyl-5-(2-thienyl)-4-isoxazolyl-amino)-6-methylpenicillanic acid,
6-(3-p-chlorophenyl)-5-methyl-4-isoxazolyl-amino)-6-methylpenicillanic acid,
6-(3-methyl-5-methylmercapto-4-isoxazolyl-amino)-6-methylpenicillanic acid,
6-(5-p-chlorophenyl)-3-methyl-4-isoxazolyl-amino)-6-methylpenicillanic acid,
6-(3-methyl-5-(o-nitrophenyl)-4-isoxazolyl-amino)-6-methylpenicillanic acid,
6-(5-isopropyl-3-methyl-4-isoxazolyl-amino)-6-methylpenicillanic acid, and
6-(3-methyl-3-(p-chlorophenyl)-4-isoxazolyl-amino)-6-methylpenicillanic acid, respectively.

EXAMPLE 259

To 100 ml. aqueous solution (pH 8.0) of 10 g. crude 6-amino-6-methylpenicillanic acid are added 8 g. freshly distilled phenylacetaldehyde. After 2 hours agitation at room temperature, 250 ml. of methyl cyclohexanone are added and the pH adjusted to 4.0 with HCl. After 30 minutes the phases are separated and the rich organic solvent is dried by azeotropic distillation of the water present. The triethylamine salt is prepared by the addition of 6.5 ml of amine.

The solution is cooled to 0°–5° and a mixture of 9.5 g. D(−)-2-phenylglycyl chloride hydrochloride in 100 ml. of methyl cyclohexanone is added over a period of 1 hour, maintaining a pH of 0°–5° C. After an additional hour agitation, 100 ml. cold phosphate buffer at pH 7.5 is added and the pH adjusted to 2.0. The solvent layer is discarded and the aqueous layer adjusted to pH 5.0. After 1 hour, filtration and drying yields 6-methyl-ampicillin.

By substituting the reaction product of sodium D(−)-α-aminophenyl acetate with methyl acetoacetate for the D(−)-2-phenylglycyl chloride hydrochloride in the foregoing procedure, 6-methyl-ampicillin is also produced.

EXAMPLES 260–269

In the procedure of Example 259, the D-(−)-2-phenylglycyl chloride is replaced with an equimolar amount of
α-(1-naphthyl)glycyl chloride,
α-(2-naphthyl)glycyl chloride,
α-(1-chloro-2-naphthyl)glycyl chloride,
α-(2-methyl-7-naphthyl)glycyl chloride,
α-(6-nitro-1-naphthyl)glycyl chloride,
α-(2,7-dibromo-3-naphthyl)glycyl chloride,
α-(4-trifluoromethyl-1-naphthyl)glycyl chloride,
α-(8-iodo-1-naphthyl)glycyl chloride,
α-(1-methoxy-2-naphthyl)glycyl chloride, and
α-(4-acetamido-1-naphthyl)glycyl chloride,
respectively, to produce
6-[α-amino-(1-naphthyl)acetamido]-6-methylpenicillanic acid,
6-[α-amino-(2-naphthyl)acetamido]-6-methylpenicillanic acid,
6-[α-amino-(1-chloro-2-naphthyl)acetamido]-6-methylpenicillanic acid,
6-[α-amino-(2-methyl-7-naphthyl)acetamido]-6-methylpenicillanic acid,
6-[α-amino-(6-nitro-1-naphthyl)acetamido]-6-methylpenicillanic acid,
6-[α-amino-(2,7-dibromo-3-naphthyl)acetamido]-6-methylpenicillanic acid,
6-[α-amino-(4-trifluoromethyl-1-naphthyl)acetamido]-6-methylpenicillanic acid,
6-[α-amino-(8-iodo-1-naphthyl)acetamido]-6-methylpenicillanic acid,
6-[α-amino-(1-methoxy-2-naphthyl)acetamido]-6-methylpenicillanic acid, and
6-[α-amino-(4-acetamido-1-naphthyl)acetamido]-6-methylpenicillanic acid, respectively.

EXAMPLE 270

10 g. triethylamine salt of 6-amino-6-methylpenicillanic acid is dissolved in 100 ml. methylene chloride. The solution is cooled to 0°–5° and 7 g. 2,6-dimethoxy benzoyl chloride is added dropwise over a period of 1½ hours, maintaining the same temperature. After an additional 30 minutes, the solution is mixed with an equal volume of cold (5°–10°) phosphate buffer (pH 7.5). To complete the hydrolysis of the intermediate, the pH is adjusted to pH 2.0 and the mixture is agitated for 15 minutes. The aqueous layer is discarded and the acid organic solvent layer is mixed with 50 ml. of cold water and neutralized to pH 7.5 with 20% sodium hydroxide. The aqueous solution is separated and concentrated into 100 ml. methyl isobutylketone. After standing overnight in the cold room, the crystals are filtered and dried to yield 6-methyl-methicillin.

EXAMPLE 271–277

In the procedure of Example 270, the phenoxyacetyl chloride is replaced by an equimolar amount of
thiophene-2-carboxylic acid chloride,
thiophene-3-carboxylic acid chloride,
furan-2-carboxylic acid chloride,
furan-3-carboxylic acid chloride,
isonicotinyl chloride.
pyrrolidinecarboxylic acid chloride, and
N-methylpiperidine-3-carboxylic acid chloride,
respectively, to produce the sodium salt of
6-(2-thiophene)carboxamidopenicillanic acid,
6-(3-thiophene)carboxamidopenicillanic acid,
6-(2-furan)carboxamidopenicillanic acid,
6-(3-furan)carboxamidopenicillanic acid,
6-isonicotinylcarboxamidopenicillanic acid,
6-pyrrolidinecarboxamidopenicillanic acid, and
6-[3-(N-methylpiperidine)]carboxamidopenicillanic acid, respectively.

EXAMPLE 278

6-Amino-6-allylpenicillanic acid

Following the procedure of Example 10, but utilizing allyl chloride in lieu of methyl chloride, the desired product is recovered.

EXAMPLE 279

6-Amino-6-cyclohexylpenicillanic acid

Utilizing the procedure of Example 10, but substituting cyclohexyl chloride in lieu of methyl chloride, the desired product is recovered.

EXAMPLE 280

N-Benzylidene-6-amino-6-allylpenicillanic acid, methyl ester

Following the procedure of Example 11, but utilizing an equivalent amount of allyl chloride in lieu of methyl iodide, the desired product is recovered.

EXAMPLE 281

6-Phenylacetamido-6-benzylpenicillanic acid

Utilizing the procedure of Example 18, but substituting benzyl chloride for methyl iodide, the desired product is recovered.

EXAMPLES 282–284

By following the procedure of Example 11, and substituting in place of the N-benzylidene-6-aminopenicillanic acid methyl ester an equivalent amount of:
N-(o-nitrobenzylidene)-6-aminopenicillanic acid,
N-(phenylethylidene)-6-aminopenicillanic acid, and
N-ethylidene-6-aminopenicillanic acid,
and an additional equivalent of sodium hydride the products obtained are:
N-(o-nitrobenzylidene)-6-amino-6-methyl-penicillanic acid,
N-(phenethylidene)-6-amino-6-methyl-penicillanic acid, and
N-(ethylidene)-6-amino-6-methyl-penicillanic acid.

What is claimed is:

1. A compound of the formula:

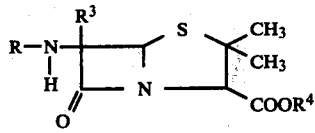

wherein $R^3$ is selected from the group consisting of lower alkyl, allyl, and benzyl; $R^4$ is selected from the group consisting of hydrogen, lower alkyl, benzyl, diphenylmethyl, trichloroethyl, and trimethylsilyl; and R is selected from the group consisting of

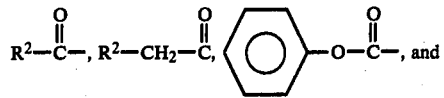

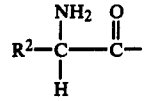

wherein $R^2$ is selected from the group consisting of thienyl, phenyl, and mono and disubstituted phenyl and thienyl wherein said substituents are selected from the group consisting of chloro, bromo, nitro, lower alkyl, and lower alkoxy; and pharmaceutically acceptable salts thereof.

2. The compound of claim 1 wherein $R^3$ is lower alkyl.

3. The compound of claim 2 wherein $R^3$ is methyl and $R^4$ is hydrogen.

4. The compound of claim 3 wherein R is selected from the group consisting of

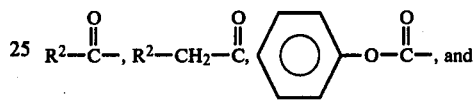

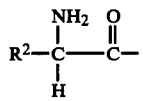

wherein $R^2$ is selected from the group consisting of phenyl and thienyl.

5. The compound of claim 4 having the name 6-phenylacetamido-6-methylpenicillanic acid.

6. The compound of claim 4 having the name 6-benzamido-6-methylpenicillanic acid.

7. The compound of claim 1 wherein $R^3$ is allyl.

8. The compound of claim 1 wherein $R^3$ is benzyl and $R^4$ is hydrogen.

9. The compound of claim 8 having the name 6-phenylacetamido-6-benzylpenicillanic acid.

10. A compound in accordance with claim 8 having the name 6-(phenoxyacetamido)-6-benzylpenicillanic acid.

11. A compound in accordance with claim 4 having the name 6-(α-aminophenylacetamido)-6-methylpenicillanic acid.

12. A compound in accordance with claim 4 having the name 6-(phenoxyacetamido)-6-methylpenicillanic acid.

13. A compound in accordance with claim 4 having the name 6-[thienylacetamido]-6-methylpenicillanic acid.

14. A compound in accordance with claim 4 having the name 6-[2-amino-thienylacetamido]-6-methylpenicillanic acid.

* * * * *